United States Patent [19]

Gootjes et al.

[11] Patent Number: 4,476,129
[45] Date of Patent: Oct. 9, 1984

[54] 4-[2-[BIS(HALOPHENYL)METHOXY]-ETHYL]-α-(SUBSTITUTED PHENYL)-1-PIPERAZINEALKANOL DERIVATIVES, PROCESSES FOR THEIR PREPARATION AND PHARMACEUTICAL PREPARATIONS CONTAINING THEM

[75] Inventors: Johan Gootjes, Heerhugowaard; Hendricus H. van de Kamp, Alphen aan de Rijn, both of Netherlands

[73] Assignee: Gist-Brocades N.V., Delft, Netherlands

[21] Appl. No.: 509,168

[22] Filed: Jun. 29, 1983

[30] Foreign Application Priority Data

Jun. 29, 1982 [NL] Netherlands ............... 8202636

[51] Int. Cl.³ ............... A61K 31/495; C07D 241/04
[52] U.S. Cl. ....................... 424/250; 544/397
[58] Field of Search ................. 544/397; 424/250

[56] References Cited

U.S. PATENT DOCUMENTS 4,202,896 5/1980 Gootjes ............... 544/397
4,265,894 5/1981 Gootjes ............... 544/397

OTHER PUBLICATIONS

Buzas et al., Chemical Abstracts, vol. 88, (1978), p. 392, 62416r, [(Benzhydryloxy)alkyl]piperazines.

Primary Examiner—Donald G. Daus
Assistant Examiner—Cecilia Shen
Attorney, Agent, or Firm—Robert E. Burns; Emmanuel J. Lobato; Bruce L. Adams

[57] ABSTRACT

The invention relates to new piperazine derivatives of the general formula

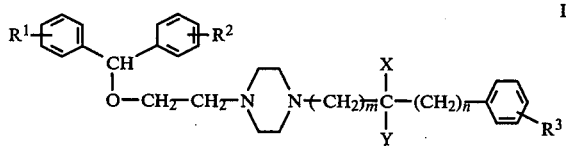

in which
R¹ and R² each represents 1, 2 or 3 halogen atoms, which may be the same or different,
R³ represents a hydrogen atom or 1, 2 or 3 halogen atoms, X represents a hydroxy, $C_{1-4}$ alkoxy, phenylcarbamoyloxy or $C_{1-4}$ alkylcarbamoyloxy group,
Y represents a hydrogen atom or a $C_{1-3}$ alkyl group, or X and Y together with the carbon atom to which they are linked represent a carbonyl group,
m is 1, 2 or 3,
n is 0 or 1, with the proviso that m+n is at most 3, and their acid addition and quaternary ammonium salts.

Other features of the invention are
processes for the preparation of compounds of formula I,
pharmaceutical preparations comprising a compound of formula I.

19 Claims, No Drawings

4-[2-[BIS(HALOPHENYL)METHOXY]-ETHYL]-α-(SUBSTITUTED PHENYL)-1-PIPERAZINEALKANOL DERIVATIVES, PROCESSES FOR THEIR PREPARATION AND PHARMACEUTICAL PREPARATIONS CONTAINING THEM

The invention relates to new therapeutically active piperazine derivatives, processes for their preparation and pharmaceutical preparations containing them.

Compounds resembling in structure the compounds of the invention are known from the Dutch patent application No. 7713817. This patent application relates to compounds of the formula

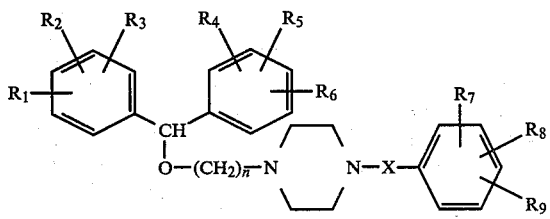

in which $R_1$–$R_9$ are the same or different and each represents a hydrogen atom, a halogen atom, a lower alkyl group or a lower alkoxy group, n is 2 or 3 and X represents a group $(CH_2)_m$ (in which m is 1, 2, 3 or 4) or a group $-CH_2-CH=CH-$ (with the methylene group linked to the piperazine ring). These compounds show dopaminergic and anticholinergic activities.

Related compounds are also known from the German patent application No. 2719246. Said application relates to compounds of the formula

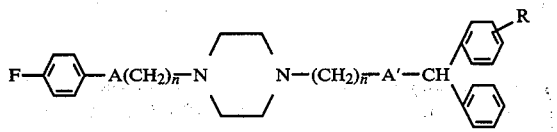

in which R represents a hydrogen or halogen atom or a methoxy, methylenedioxy, nitro, trifluoromethyl or methyl group, n and n' are 2 or 3, A represents a C=O— or CHOH group and A' represents an oxygen atom or a $CH_2$ group. These compounds are antiemetics and spasmolytics.

Some compounds of the invention are structurally closely related to the known compounds. Surprisingly however they show a considerable difference in pharmacological activity with said known compounds.

The new piperazine derivatives of the invention have the general formula I

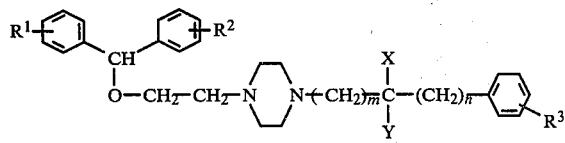

in which
$R^1$ and $R^2$ each represents 1, 2 or 3 the same or different halogen atoms, $R^3$ represents a hydrogen atom or 1, 2 or 3 halogen atoms, X represents a hydroxy-, $C_{1-4}$ alkoxy-, phenylcarbamoyloxy-, or $C_{1-4}$ alkylcarbamoyloxy group, Y represents a hydrogen atom or a $C_{1-3}$ alkyl group, or X and Y together with the carbon atom to which they are linked represent a carbonyl group, m is 1, 2 or 3, n is 0 or 1, with the provision that m+n is at most 3.

The invention also includes acid addition salts and quaternary ammonium salts of the compounds of formula I.

Suitable meanings of $R^1$ and $R^2$ are fluorine, chlorine and bromine. Very suitable are those compounds in which $R^1$ and $R^2$ each represents 1 or 2 halogen atoms, the fluorine atom being preferred. Most preferred compounds are those in which $R^1$ and $R^2$ each represents one fluorine atom, particularly the compounds in which both fluorine atoms are in the para-position.

Suitable meanings of $R^3$ are hydrogen, fluorine, chlorine or bromine. When $R^3$ is halogen, fluorine and particularly one fluorine atom is preferred. $R^3$ is preferably hydrogen or para-fluorine.

Suitable meanings of X are hydroxy, methoxy, ethoxy, n-propoxy, isopropoxy, n-butoxy, isobutoxy, methylcarbamoyloxy and ethylcarbamoyloxy.

Suitable meanings of Y are hydrogen, methyl, ethyl, n-propyl and isopropyl. X is preferably hydroxy, or together with Y, oxygen. The most preferred meaning of X is hydroxy. When X is hydroxy, Y is preferably hydrogen, methyl or ethyl and particularly hydrogen.

Suitable values of m are 1, 2 or 3, and preferably 1 or 2.

A suitable group of compounds of formula I is that of the formula

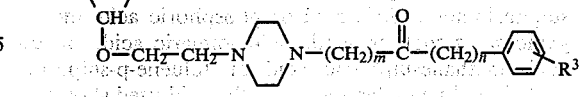

in which $R^3$, m and n are as hereinbefore defined. Preferably $R^3$ is hydrogen or 4-fluorine. A suitable compound in this group is the one in which $R^3$ is hydrogen and m and n are 1.

A group of preferred compounds of formula I is that with the formula

in which $R^3$, Y m and n are as hereinbefore defined. Preferably $R^3$ is hydrogen or 4-fluorine. Y is preferably hydrogen, methyl or ethyl and particularly hydrogen. Particularly preferred are those compounds of this group in which $R^3$ is hydrogen or 4-fluorine, Y is hydrogen, m is 2 and n is 0, and also the compound in which Y and $R^3$ are hydrogen and m and n are 1.

Another group of suitable compounds of formula I is that of the formula

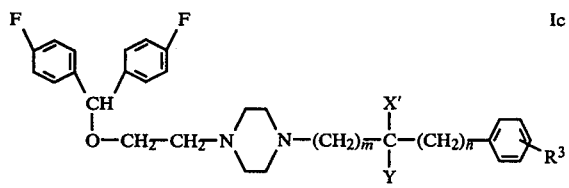

Ic in which $R^3$, Y, m and n are as hereinbefore defined and X' is alkoxy or alkylcarbamoyloxy.

In view of their pharmacological properties the following compounds are particularly preferred:

a. 4-[2-[bis(4-fluorophenyl)methoxy]ethyl]-α-(4-fluorophenyl)-1-piperazinepropanol
b. 4-[2-[bis(4-fluorophenyl)methoxy]ethyl]-α-(phenylmethyl)-1-piperazineëthanol
c. 4-[2-[bis(4-fluorophenyl)methoxy]ethyl]-α-phenyl-1-piperazinepropanol
d. 4-[2-[bis(4-fluorophenyl)methoxy]ethyl]-α-phenyl-1-piperazineëthanol
e. 1-[4-[2-bis(4-fluorophenyl)methoxy]ethyl]-1-piperazinyl]-3-phenyl-2-propanone
f. 4-[2-[bis(4-fluorophenyl)methoxy]ethyl]-α-phenyl-1-piperazinebutanol
g. 4-[2-[bis(4-fluorophenyl)methoxy]ethyl]-α-(4-fluorophenyl)-α-methyl-1-piperazinepropanol
h. 4-[2-[bis(4-fluorophenyl)methoxy]ethyl]-α-phenyl-α-methyl-1-piperazinepropanol
i. 4-[2-[bis(4-fluorophenyl)methoxy]ethyl]-α-ethyl-α-phenyl-1-piperazinepropanol and the pharmaceutically acceptable acid addition and quaternary ammonium salts of these compounds.

The compounds a, b and c are most preferred.

The compounds described above of formula I can exist as free bases or in the form of acid addition salts or quaternary ammonium salts. Suitable acids for the preparation of acid addition salts are for instance inorganic acids, such as hydrochloric acid, hydrobromic acid, sulphuric acid, nitric acid or phosphoric acid and organic acids such as acetic acid, fumaric acid, tartaric acid, methanesulphonic acid or toluene-p-sulphonic acid. It will be understood that the acid used should be pharmaceutically acceptable. Preferred acid addition salts are those derived from hydrochloric acid.

An example of a quaternary addition salt is the methiodide.

The compounds of formula I may contain one or more asymmetric carbon atoms, which gives rise to the existence of different stereoisomeric forms.

The compounds of the invention as represented by formula I, include free bases, acid addition salts, quaternary ammonium salts, racemates, separated optical isomers as well as their mixtures.

The compounds of the invention can also be obtained in the form of solvates, such as hydrates. The acid addition salts are obtained in crystalline form.

The piperazine derivatives of general formula I possess useful pharmacological properties. They show a strong specific dopaminergic activity and low toxicity. The compounds are therefore useful in the treatment of Parkinson's disease and of pathological disorders caused by increased prolactine production (galactorrhea, excessive puerpural lactation, hypogonadism, infertility) and with excessive excretion of growth hormones (acromegaly). The dopaminergic activity was assessed both in animal tests (stereotyped behaviour, decrease of prolactine level) and in vitro (inhibition re-uptake of dopamine by striatal synaptosomes). Further it was established that the compounds have an affinity to dopamine receptors.

The doses to be used will depend on the disorder to be treated. Suitable daily doses for oral administration for adults are (i) in parkinsonism: 50–200 mg, (ii) in acromegaly: 20–40 mg, and (iii) in disorders caused by prolactine 5–25 mg.

The examination of the compounds of the invention included the following tests.

A. Inhibition of re-uptake of dopamine by striatal synaptosomes.

The re-uptake process is the most important physiological mechanism causing inactivation of neurotransmitters like dopamine, which are released into the synaptic cleft by a nervous impulse. Inhibition of the dopamine uptake will lead to increased concentration of dopamine in the synaptic cleft and potentiation of the dopamine effect on the post-synaptic receptor. This inhibition was examined in vitro by incubation of synaptosomes of the corpus striatum of the rat with radioactive labelled dopamine, as described by P. van der Zee and W. Hespe, Neuropharmacol. 17, 483–490 (1978). Measurements were made of the concentration of the test compound giving 50% inhibition of the uptake ($IC_{50}$).

B. Affinity to dopamine receptors.

The affinity of the compounds to the dopamine receptors in a membrane fraction of the corpus striatum of the rat was determined as described by D. R. Burt et al., Mol. Pharmacol., 12, 800–812 (1976), dopamine and the dopamine antagonist haloperiodol being used as radioactive labelled ligands. The IC50-value is the concentration of the piperazine derivatives necessary to inhibit the specific binding of dopamine, or haloperiodol for 50%.

C. Stereotypy in the rat.

The stereotyped behavior appearing in the rat after administration of centrally active dopaminergic substances can be regarded as a relevant test for antiparkinson agents. The dopaminergic D-2 receptors, the stimulation of which is the cause of stereotype, are also the dopamine receptors showing insufficient activity in Parkinson's disease (M. Schachter c.s., Nature, 286, 157–159 (1980)).

The tests were carried out with female Wistar rats under conditions with a low level of stimuli. The behaviour of the rats was observed on 15, 30, 60, 120, 180, 240 and 300 minutes after administration of the substance, the following parameters being considered:

| | |
|---|---|
| 1. sniffing | 8. increased locomotor activity |
| 2. licking | 9. bizarre social behaviour |
| 3. grooming | 10. tremor |
| 4. standing upright | 11. increased leg tonus |
| 5. rocking of the head | 12. straub's tail |
| 6. gnawing | 13. exophtalmus |
| 7. self-mutilation | 14. ptosis |

The total impression of the intensity of stereotypy was noted according to the following rating:

| | |
|---|---|
| 0 = absent | 2 = moderate |

1 = weak    3 = strong

For each dose a group of four rats was used, so that the total score for the seven observations was maximally 7×4×3=84. With the aid of regression-analysis the dose was calculated giving 50% of the maximal effect (ED50-value).

The results of the tests are shown in Tables 1 and 2. In the compounds tested $R^1 = R^2 = 4$-F.

TABLE 1

Biochemical tests
IC50 in nM

| Cpd. | $X^1$ | Y | $R_3$ | m | n | Uptake dopamine | Receptor binding dopamine | haloperidol |
|---|---|---|---|---|---|---|---|---|
| 1 | OH | H | H | 1 | 0 | 26.5 | 46.7 | 780 |
| 2 | OH | H | H | 2 | 0 | 1.3 | 13.3 | 307 |
| 3 | OH | H | 4-F | 2 | 0 | 8.2 | 8.7 | 610 |
| 4 | OH | H | H | 1 | 1 | 5.4 | 30.5 | 546 |
| 5 | OH | CH$_3$ | H | 2 | 0 | 2.4 | 22.3 | 283 |
| 6 | OH | CH$_3$ | 4-F | 2 | 0 | 6.7 | 32.3 | 277 |
| 7 | OH | C$_2$H$_5$ | H | 2 | 0 | 22.1 | 63 | 361 |
| 8 | OH | H | H | 3 | 0 | 3.4 | 4.0 | 445 |
| 9 | OH | H | 4-F | 3 | 0 | 2.8 | 18.1 | 492 |
| 10 | O | | H | 1 | 0 | 28.3 | 55 | 524 |
| 11 | O | | H | 2 | 0 | 39.7 | 80.3 | 268 |
| 12 | O | | 4-F | 2 | 0 | 35.4 | 180 | 467 |
| 13 | O | | H | 1 | 1 | 27.0 | 76 | 545 |
| 14 | O | | H | 3 | 0 | 2.5 | 15.5 | 23.3 |
| 15 | O | | 4-F | 3 | 0 | 5.2 | 291 | 19.0 |
| 16 | CH$_3$O | H | H | 2 | 0 | 13.2 | 50 | 523 |
| 17 | Meca | H | H | 2 | 0 | 4.9 | 27.2 | 97.3 |
| 18 | Eca | H | H | 2 | 0 | 2.4 | 16.9 | 216 |
| 19 | Pheca | H | H | 2 | 0 | 3.3 | 43.4 | 302 |

[1]Meca = methylcarbamoyloxy
Eca = ethylcarbamoyloxy
Pheca = phenylcarbamoyloxy

TABLE 2

Sterotyped behaviour

| Compound | ED50 in mg/kg p.o. |
|---|---|
| 1 | 17.5 |
| 2 | 1.5 |
|  | 3.1 |
| 3 | 1.7 |
|  | 2.3 |
|  | 1.3 |
| 4 | ~6 |
| 5 | 14.0 |
| 6 | 11.4 |
| 7 | 26.0 |
| 8 | 6.2 |
|  | 4.6 |
| 9 | <<5.0 |
| 11 | <5.5 |
| 12 | 5.5 |
| 13 | 9.1 |
| 14 | 18.0 |
| 15 | >46 |
| 16 | 4.6 |
| 17 | 4.3 |
|  | 7.2 |
| 18 | 11.2 |
| bromocriptine | 25.3 |
| piribedil | 99.5 |

The compounds of formula I, as well as their salts, can be prepared by methods which are known for the preparation of this type of compounds and by analogous methods. A number of these methods are described in the Dutch patent application 7713817. It should be noted that in the compounds of formula I the symbol X contains an oxygen function, so that the methods described in the said patent application only can be applied if the oxygen function (or an other functional group) will not be affected.

The invention also relates to the preparation of the compounds of formula I and its salts.

According to an embodiment of the invention the piperazine derivatives of formula I are prepared by reacting an ether of the formula

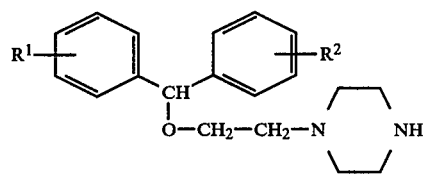

in which $R^1$ and $R^2$ are as hereinbefore defined, with a compound of the formula

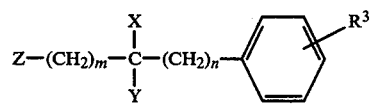

in which Z represents a halogen atom (preferably chlorine or bromine) or an other acid residue of a reactive ester like toluene-p-sulfonyloxy and the other symbols are as hereinbefore defined.

The reaction is preferably carried out by refluxing a solution of the compounds in an inert organic solvent like methyl-isobutylketone or xylene. Preferably the reaction is carried out in the presence of a base, such as potassium carbonate or a tertiary amine (such as triethylamine).

According to another embodiment of the invention the piperazine derivatives of formula I in which X is a hydroxyl group and Y a hydrogen atom and the other symbols are as hereinbefore defined, are prepared by reducing the corresponding compound in which X and Y together with the carbon atom to which they are linked form a carbonyl group and the other symbols are as hereinbefore defined, i.e. a compound of the formula

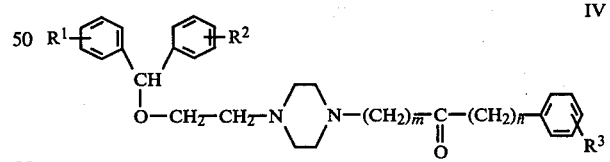

A suitable reduction agent is sodium borium hydride. Preferably the reaction is carried out in an organic solvent such as ethanol.

According to another embodiment of the invention the piperazine derivatives of formula I in which X is a hydroxyl group and Y an alkyl group with 1 to 3 carbon atoms and the other symbols are as hereinbefore defined, are prepared by reacting a compound of formula IV with a compound of formula $$Y-Mg-Hal \qquad (V)$$

in which Hal represents a chlorine-, bromine- or (preferably iodine atom, and hydrolyzing the complex obtained.

The reaction is preferably carried out under conditions generally favourable for Grignard reactions.

A suitable method is for example to form the compound of formula V by refluxing an alkyl halide in an ether (for instance diethyl ether) with magnesium and subsequently reacting the alkyl magnesium halide with the compound of formula IV by refluxing in a solvent, if desired with a higher boiling point, such as tetrahydrofuran. The reaction is preferably carried out under an inert gas atmosphere. The hydrolysis of the complex obtained can be carried out for example by means of an ammoniumchloride solution.

According to another embodiment of the invention the piperazine derivatives of formula I in which X is a hydroxyl group and the other symbols are as hereinbefore defined, may be prepared by reacting with each other, compounds of the formulae

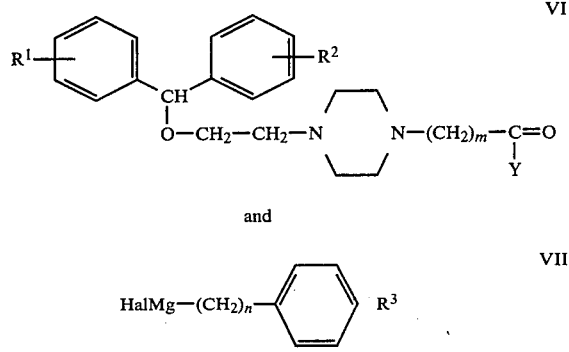

in which formulae the symbols are as hereinbefore defined and hydrolyzing the complex obtained. The reaction conditions mentioned for the reaction between compounds of formulae IV and V, are also here the most suitable.

According to another embodiment of the invention the piperazine derivatives of formula I in which X is an alkylcarbomoyloxy group with 1–4 carbon atoms in the alkyl part or a phenylcarbamoyloxy group and the other symbols are as hereinbefore defined, may be prepared by reacting the corresponding compound in which X is an hydroxyl group, i.e. a compound of the formula

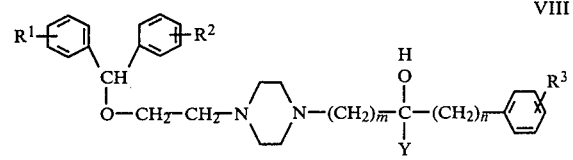

with an isocyanate of the formula

RNCO  IX in which R represents an alkyl group with 1–4 carbon atoms or a phenyl group.

The reaction is preferably carried out by refluxing in an inert organic solvent, such as toluene or xylene.

According to another embodiment of the invention the compounds of formula I may be prepared by reacting a compound of the formula

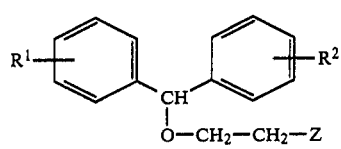

in which the symbols are as hereinbefore defined, with a piperazine derivative with the formula

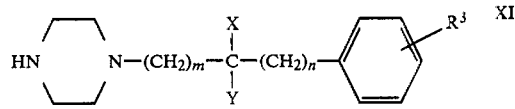

in which the symbols are as hereinbefore defined.

The reaction is preferably carried out under conditions as described for the reaction between compounds of formulae II and III.

According to another embodiment of the invention the piperazine derivatives of formula I in which X represents an alkoxy group with 1–4 carbon atoms, an alkylcarbamoyloxy group with 1–4 carbon atoms in the alkyl part or a phenylcarbamoyloxy group or X and Y together with the carbon atoms to which they are linked represent a carbonyl group and the other symbols are as hereinbefore defined, may be prepared by reacting a compound of formula

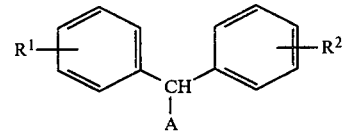

in which A represents a hydroxyl group, a halogen atom (preferably chlorine or bromine) or a group OM (in which M is an alkalimetal atom, preferably potassium or sodium) and the other symbols are as hereinbefore defined, with a compound of formula

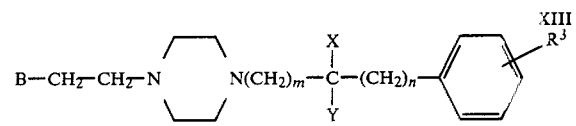

in which B represents (i) a hydroxyl group or a halogen atom when A is a hydroxyl group or (ii) a hydroxyl group or a group OM (as hereinbefore defined) when A is a halogen atom or (iii) a halogen atom when A is a group OM, and the other symbols are as hereinbefore defined.

In most cases the reaction is preferably carried out in an inert organic solvent such as benzene or toluene. When A and B both are hydroxyl groups, it is advantageous to carry out the reaction in the presence of an acid which is not volatile at the reaction temperature, for instance toluene-p-sulphonic acid. When A is a hydroxyl group and B a halogen atom, or conversely, the reaction is preferably carried out in the presence of a base, for instance an excess of the compound of formula XIII, sodium carbonate or a tertiary amine such as triethylamine.

According to another embodiment of the invention the piperazine derivatives of formula I in which is a hydroxyl group, an alkoxy group with 1-4 carbon atoms, an alkylcarbamoyloxy group with 1-4 carbon atoms in the alkyl part or a phenylcarbamoyloxy group and the other symbols are as hereinbefore defined, may be prepared by reacting a compound of formula II with an aldehyde of the formula

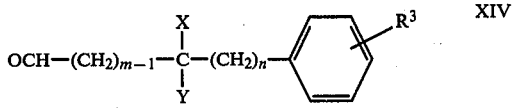
XIV in which the symbols are as hereinbefore defined, and reducing the compound obtained. Preferably the compounds of formulae II and XIV are reacted with each other in an inert organic solvent under reducing comditions, for instance in the presence of sodium cyanoborium hydride or of hydrogen with a suitable catalyst such as Raney-nickel.

According to another embodiment of the invention the piperazine derivatives of formula I in which X is a hydroxyl group or an alkoxy group with 1-4 carbon atoms, may be prepared by reducing a compound of the formula

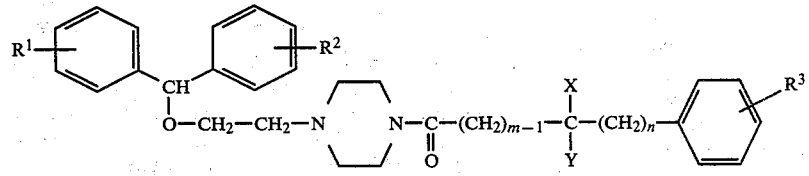
XV or a compound of the formula

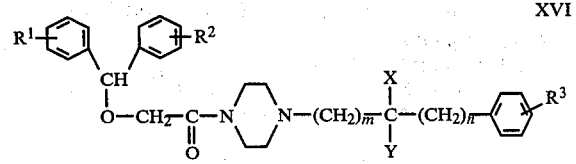
XVI in which formulae the symbols are as hereinbefore defined. Preferably the reduction is carried out in an inert organic solvent such as diethyl ether or tetrahydrofuran with a reduction agent such as lithium aluminium hydride.

According to another embodiment of the invention the piperazine derivatives of formula I in which X and Y together with the carbon atom to which they are linked represent a carbonyl group and the other symbols are as hereinbefore defined, may be prepared by oxidizing carefully the corresponding compound in which X is a hydroxyl group and Y a hydrogen atom.

According to another embodiment of the invention the piperazine derivatives of formula I in which X and Y together with the carbon atom to which they are linked form a carbonyl group and the other symbols are as hereinbefore defined, may be prepared by reacting a cyanide of the formula

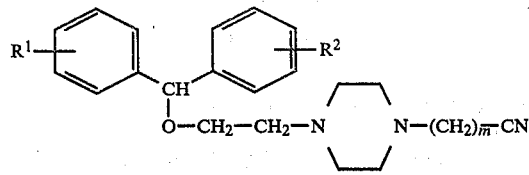
XVII with a compound of the formula VII and hydrolyzing the complex obtained.

According to another embodiment of the invention the piperazine derivatives of formula I in which X is a hydroxyl group, may be prepared by alkaline hydrolysis of a compound of the formula

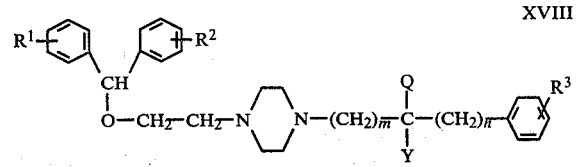
XVIII in which Q represents a halogen atom, an alkylcarbonyloxy-, a phenylcarbonyloxy- or a phenylalkylcarbonyloxy group and the other symbols are as hereinbefore defined.

The preparation of the compounds according to the invention is illustrated by the following examples. The structures were confirmed by the IR- en NMR-spectra. The NMR-spectra were measured in 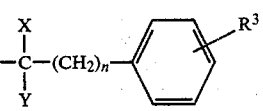, which also served as a standard substance ($\delta = 2.49$ ppm). The NMR-figures mentioned are chemical shifts in ppm.

EXAMPLE I

A Grignard solution was prepared by adding 11.4 g (0.08 mol) methyl iodide in 100 ml of anhydrous diethyl ether under a nitrogen atmosphere to 2 g (0.08 at) of magnesium, after which the reaction mixture was refluxed for one hour. At the reflux temperature 100 ml of anhydrous tetrahydrofuran and a solution of 4.5 g (0,01 mol) of 3-[4-[2-[bis(4-fluorophenyl)methoxy]ethyl]-1-piperazinyl]-1-phenyl-1-propanone in 100 ml of anhydrous tetrahydrofuran were successively added dropwise. After two hours refluxing, the reaction mixture was poured out into a mixture of an ammonium chloride solution and ice, after which the mixture was saturated with sodium chloride. The organic layer was separated off, washed with salt solution and the liquid was evaporated. The residue was taken up in diethyl ether, and the solution was carefully acidified with an ethereal solution of hydrogen chloride to pH=3. The precipitate obtained of 4-[2-[bis(4-fluorophenyl)methoxy]ethyl)]-α-phenyl-α-methyl-1-piperazinepropanol dihydrochloride was filtered off, dried and crystalized once from a mixture of methanol and diethyl ether.

Melting point 202°–203° C.

NMR: 1.46 (s, 3H), 2.05–2.6 (m, 2H), 2.7–4.1 (m, 14H; br.s. at 3.62), 5.61 (s, 1H), 6.95–7.7 (m, 13H).

EXAMPLE II

Using the procedure of Example I, the compound 4-[2-[bis-(4-fluorophenyl)methoxy]ethyl]-α-(4-fluorophenyl)-α-methyl-1-piperazinepropanol dihydrochloride was obtained from 3-[4-[2-[bis(4-fluorophenyl)methoxy]ethyl]-1-piperazinyl]-1-(4-fluorophenyl)-1-propanone, methyl iodide and magnesium.

Melting point 187.5°–189° C.

NMR: 1.45 (s, 3H), 1.95–2.6 (m, 2H), 2.7–3.9 (m, 14H; br.s. by 3.62), 5.6 (s, 1H), 6.9–7.7 (m, 12H).

EXAMPLE III

In a similar way as described in Example I the compound 4-[2-[bis(4-fluorophenyl)methoxy]ethyl]-α-ethyl-α-phenyl-1-piperazinepropanol dihydrochloride was obtained from 1-[4-[2-[bis(4-fluorophenyl)methoxy]ethyl]-1-piperazinyl]-3-pentanone, bromobenzene and magnesium.

Melting point 194°–195° C.

NMR: 0.64 (t, 3H), 1.76 (q, 2H), 2.1–2.75 (m, 2H), 2.85–3.9 (m, 14H; br.s. at 3.61), 5.61 (s, 1H), 6.95–7.7 (m, 13H).

The first mentioned starting product was prepared in the form of its dihydrochloride by the following method:

A mixture of 12 g (0.036 mol) of 1-[2-[bis(4-fluorophenyl)methoxy]ethyl]piperazine, 8.7 g (0.072 mol) of 1-chloro-3-pentanone and 10 g of powdered potassium carbonate in 200 ml of anhydrous xylene was refluxed for 6 hours with stirring. The reaction mixture was washed with water, dried and the liquid was evaporated. The residue was taken up in 2-propanol after which the solution was carefully acidified with a solution of hydrogen chloride in diethyl ether to pH=3. The dihydrochloride was filtered off, dried and crystallized consecutively once from a mixture of 2-propanol and diethyl ether and once from a mixture of 2-propanol and methanol.

Melting point 173.5–174.5

EXAMPLE IV 1 g (0.025 mol) of sodium borohydride was added in small portions at 20°–30° C. to a solution of 7.5 g (0.015 mol) of 3-[4-[2-[bis(4-fluorophenyl)methoxy]ethyl]-1-piperazinyl]-1-(4-fluorophenyl)-1-propanone in 75 ml of ethanol. After two hours refluxing, the solvent was evaporated. Water and chloroform were added to the residue. The chloroform layer was separated off, washed with water, dried and the solvent was distilled off. The residue was taken up in a mixture of diethyl ether and ethanol after which the solution was carefully acidified to pH=3 with a solution of hydrogen chloride in diethyl ether.

The precipitate of 4-[2-[bis(4-fluorophenyl)methoxy]ethyl]-α-(4-fluorophenyl)-1-piperazinepropanol dihydrochloride was filtered off and crystallized once from 2-propanol.

Melting point 189°–189.5° C.

NMR: 1.8–2.4 (m, 2H), 2.9–4.0 (m, 14H; br.s. at 3.71), 4.73 (t, 1H), 5.63 (s, 1H), 6.95–7.7 (m, 12H).

EXAMPLE V

Using similar procedures as described in Example IV the following compounds were obtained from the corresponding ketones:

a. 4-[2-[bis(4-fluorophenyl)methoxy]ethyl]-α-phenyl-1-piperazinepropanol dihydrochloride, crystallized from methanol, melting point 211°–212° C.

NMR: 1.75–2.35 (m, 2H), 2.9–4.1 (m, 14H; br.s. at 3.69), 4.71 (t, 1H), 5.63 (s, 1H), 6.95–7.7 (m, 13H).

b. 4-[2-[bis(4-fluorophenyl)methoxy]ethyl]-α-phenyl-1-piperazinebutanol dihydrochloride, crystallized from a mixture of methanol and diethyl ether, melting point 196° C.

NMR: 1.5–1.9 (m, 4H), 2.9–4.0 (m, 14H; br.s. at 3.64), 4.57 (t, 1H), 5.62 (s, 1H), 6.95–7.7 (m, 13H).

c. 4-[2-[bis(4-fluorophenyl)methoxy]ethyl]-α-(4-fluorophenyl)-1-piperazinebutanol dihydrochloride, crystallized from a mixture of methanol and diethylether, Melting point 196.5°–197.5° C.

NMR: 1.5–1.9 (m, 4H), 2.8–3.9 (m, 14H; br.s. at 3.61), 4.59 (t, 1H), 5.63 (s, 1H), 6.59–7.7 (m, 12H).

d. 4-[2-[bis(4-fluorophenyl)methoxy]ethyl]-α-phenyl-1-piperazineëthanol dihydrochloride, crystallized from methanol, melting point 211°–211.5° C.

NMR: 3.2–4.1 (m, 14H; br.s. at 3.72), 5.24 (t, 1H), 5.64 (s, 1H), 7.2–7.7 (m, 13H).

EXAMPLE VI

A mixture of 6 g (0.018 mol) of 1-[2-[bis(4-fluorophenyl)methoxy]ethyl]piperazine, 6.6 g (0.036 mol) of 4-chloro-1-phenyl-1-butanone and 5 g of powdered potassium carbonate in 100 ml of methyl isobutyl ketone was refluxed for 6 hours with stirring. The reaction mixture was concentrated by evaporation of the solvent and water and diethyl ether were added to the residue, after which the ethereal layer was separated off, washed with water, dried on sodium sulfate and the solvent was evaporated. The residue obtained was purified by columnchromatography (silicagel, eluent: chloroform/methanol 9:1). The proper fractions were concentrated and the residue was taken up in anhydrous diethyl ether, after which the solution was carefully acidified with a solution of hydrogen chloride in diethyl ether to pH=2. The precipitate obtained of 4-[4-[2-[bis(4-fluorophenyl)methoxy]-ethyl]-1-piperazinyl]-1-phenyl-1-butanone dihydrochloride was filtered off and crystallized once from 2-propanol.

Melting point 210°–211° C.

NMR: 1.80–2.40 (m, 2H), 2.95–4.10 (m, 16H; br.s. at 3.74), 5.62 (s, 1H), 6.95–8.20 (m, 13H).

EXAMPLE VII

By a similar method as described in Example VI the compound 4-[4-[2bis(4-fluorophenyl)methoxy]ethyl]-1-piperazinyl]-1-(4-fluorophenyl)-1-butanone dihydrochloride was obtained from 1-[2-[bis(4-fluorophenyl)methoxy]ethyl]piperazine and 4-chloro-1-(4-fluorophenyl)-1-butanone.

Melting point 210°–210.5° C.

NMR: 1.8–2.35 (m, 2H), 3.00–4.10 (m, 16H; br.s. at 3.72), 5.62 (s, 1H), 6.95–8.20 (m, 12H).

EXAMPLE VIII

1-[2-[Bis(4-fluorophenyl)methoxy]ethyl]piperazine and 3-chloro-1-(4-fluorophenyl)-1-propanone were reacted with each other as decribed in Example VI. After evaporation of the solvent, water and chloroform were added. The working up was further as in Example VI, except that the residue of the column fraction was taken up in ethanol. 3-[4-[2-bis(4-fluorophenyl)methoxy]e- thyl]-1-piperazinyl)-1-(4-fluorophenyl)-1-propanone dihydrochloride was obtained.

Melting point 162.5°–163.5° C.

NMR: 3.74 (br.s., 16H), 5.66 (s, 1H), 6.95–8.20 (m, 12H).

EXAMPLE IX

In a similar way as described in Example VIII 2-[4-[2-[bis(4-fluorophenyl)methoxy]ethyl]-1-piperazinyl]-1-phenylethanone dihydrochloride was obtained from 1-[2-[bis(4-fluorophenyl)methoxy]ethyl]piperazine and 2-chloroacetophenone. The residue of the column fractions was taken up in 2-propanol. The end product was crystallized from a mixture of ethanol and diethyl ether.

Melting point 200°–202° C.

NMR: 3.3–4.0 (m, 12H; br.s. at 3.73), 5.16 (s, 2H), 5.63 (s, 1H), 6.95–8.2 (m, 13H).

EXAMPLE X

A mixture of 6 g (0.018 mol) of 1-[2-[bis(4-fluorophenyl)methoxy]ethyl]piperazine, 6.1 g (0.036 mol) of 3-chloro-1-phenyl-1-propanone and 5 g of powdered potassium carbonate in 100 ml of methylisobutylketone was refluxed for 1¼ hour with stirring. The solvent was evaporated and water and chloroform were added to the residue, after which the chloroform layer was separated off, washed with water, dried on sodium sulfate and concentrated. The residue obtained was dissolved in ethanol after which a solution of hydrogen chloride in diethyl ether was added to pH=2. The precipitate, consisting of 3-[4-[2-[bis(4-fluorphenyl)methoxy]ethyl]-1-piperazinyl]-1-phenyl-1-propanone dihydrochloride, was filtered off and dried in vacuo at 60° C.

Melting point 175°–177° C.

NMR: 3.72 (br.s. 16H), 5.62 (s, 1H), 6.95–8.20 (m, 13H).

EXAMPLE XI

A mixture of 6 g (0.018 mol) of 1-[2-[bis(4-fluorophenyl)methoxy]ethyl]piperazine, 7.7 g (0.036 mol) of α-(bromomethyl)benzene-ethanol[1]) and 5 g of powdered potassium carbonate in 100 ml of anhydrous xylene was refluxed for 8 hours with stirring. The reaction mixture was washed with water, dried on sodium sulphate and concentrated. The residue was taken up in 2-propanol, after which the solution was carefully acidified with a solution of a hydrogen chloride in diethyl ether to pH=3. The precipitate formed, consisting of 4-[2-[bis(4-fluorophenyl)methoxy]ethyl]-α-(phenylmethyl)-1-piperazineëthanol dihydrochloride, was filtered off, dried in vacuo at 60° C. and crystallized once from methanol.

Melting point 218°–220° C.

NMR: 2.77 (d, 2H), 3.0–4.05 (m, 14H; br.s. at 3.71), 4.45–5.0 (m, 1H), 5.62 (s, 1H), 6.9–7.7 (m, 13H).

EXAMPLE XII

A mixture of 6 g (0.018 mol) of 1-[2-[bis(4-fluorophenyl)methoxy]ethyl]piperazine, 7.7 g (0.036 mol) of 1-bromo-3-phenyl-2-propanone[1]) and 5 g of powdered potassium carbonate in 100 ml of anhydrous xylene was refluxed for eight hours with stirring. The reaction mixture was washed with water, dried and the solvent was evaporated. The residue was taken up in 2-propanol, after which the solution was carefully acidified with a solution of hydrogen chloride in diethyl ether to pH=3.

[1]) prepared as described by R. H. Good and G. Jones, J. Chem. Soc. C 1970, 1938–45.

The precipitate obtained of 1-[4-[2-[bis(4-fluorophenyl)methoxy]ethyl]-1-piperazinyl]-3-phenyl-2-propanone dihydrochloride was filtered off, dried in vacuo at 60° C. and boiled up once in a mixture of methanol and dimethylformamide. After cooling, the solid substance was filtered off and dried.

Melting point 214.5°–216.5° C.

NMR: 3.0–4.25 (m, 12H; br.s. at 3.65), 3.88 (s, 2H), 4.48 (s, 2H), 5.61 (s, 1H), 6.9–7.75 (m, 13H).

EXAMPLE XIII 2.9 ml of methyl isocyanate were added dropwise at 30° C. to a solution of 5.6 g (0.012 mol) of 4-[2-[bis-(fluorophenyl)-methoxy]ethyl]-α-phenyl-1-piperazinepropanol in 100 ml of anhydrous toluene. After one hour stirring at 30° C. the reaction mixture was refluxed for 2 hours and than the solvent was evaporated. The residue was taken up in 2-propanol, after which the solution was acidified carefully with a solution of maleic acid in diethyl ether to pH=3. The precipitate obtained of methylcarbaminic 3-[4-[2-[bis(4-fluorophenyl)methoxy]ethyl]-1-piperazinyl]-1-phenylpropyl]-ester (Z)-2-butendioate (1:2) was filtered off, dried and crystallized once from methanol.

Melting point 177°–178° C.

NMR: 1.7–2.4 (m, 2H), 2.53 (s, 3H), 2.7–3.2 (m, 14H; br.s. at 2.94), 3.58 (t, 2H), 5.54 (s, 1H), 5.64 (t, 1H), 6.14 (s, 4H), 6.95–7.6 (m, 13H).

EXAMPLE XIV

In the same was as described in Example XIII, using instead of methyl isocyanate respectively phenyl isocyanate and ethyl isocyanate, the following compounds were prepared a. Phenylcarbaminic[3-[4-[2-[bis(4-fluorophenyl)methoxy]ethyl]-1-piperazinyl]-1-phenylpropyl]ester (Z)-2-butenedioate (1:2).

Melting point 178°–179° C.

NMR: 1.85–2.35 (m, 2H), 2.6–3.2 (m, 12H); br.s. at 2.97), 3.57 (t, 2H), 5.54 (s, 1H), 5.77 (t, 1H), 6.14 (s, 4H), 6.9–7.6 (m, 18H).

b. Ethylcarbaminic[3-[4-[2-[bis(fluorophenyl)methoxy]ethyl]-1-piperazinyl]-1-phenylpropyl]ester (Z)-2-butenedioate (1:2).

Melting point 184° C.

NMR: 0.99 (t, 3H), 1.7–2.3 (m, 2H), 2.6–3.3 (m, 14H); br.s. at 2.95), 3.57 (t, 2H), 5.50 (s, 1H), 5.62 (t, 1H), 6.15 (s, 4H), 6.8–7.8 (m, 13H).

EXAMPLE XV 4.6 g (0.2 mol) of (3-bromo-1-methoxypropyl)benzene (prepared as described by R. T. Lalonde and P. B. Ferrara—J. Org. Chem. 37, 2502–05 (1972)) were added dropwise at reflux temperature to a mixture of 6 g (0.018 mol) of 1-[2-[bis(4-fluorophenyl)methoxy]ethyl]piperazine and 3 g of powdered potassium carbonate in 50 ml of ethanol. After one hour refluxing, another 4.6 g of (3-bromo-1-methoxypropyl)benzene were added at reflux temperature to make the reaction complete. After another hour of refluxing the reaction mixture was concentrated, the residue was taken up in diethyl ether and the solution was filtered over infusorial earth and concentrated. The residue now obtained was purified by column chromatography (silica gel, eluent chloroform/methanol 19:1). The base obtained was taken up in diethyl ether, after which a solution of hydrogen chloride in diethyl ether was added to pH=3.

The precipitated 1-[2-[bis-(4-fluorophenyl)methoxy]ethyl]-4-(3-phenyl-3-methoxypropyl)piperazine dihydrochloride was boiled up in acetone and crystallized from a mixture of 2-propanol and diethylether.

Melting point 189.5°–190° C.

NMR: 1.85 (m, 2H), 3.09 (s, 3H), 3.0–4.1 (m, 12H); br.s. at 3.69), 4.34 (t, 2H), 5.62 (s, 1H), 6.9–7.65 (m, 14H).

The invention also includes pharmaceutical preparations which contain as active ingredient at least one of the piperazine derivatives of formula I or an acid addition of quaternary ammonium salt thereof in combination with one or more auxiliary agents commonly used in pharmacy. The preparations may take any of the forms customarily employed for administration of therapeutic substances. In preparations for oral administration a suitable amount of active substance is between 5 and 100 mg. As possible forms for oral administration there may be mentioned tablets, pills, capsules, suspensions, emulsions, syrups and elixirs. Examples of other forms of administration are suppositoria and injection liquids. The invention also includes dry formulations which can be converted into a solution or suspension suitable for oral or parenteral administration by addition of liquid. Such dry formulations can for instance be obtained by freeze-drying of the liquid preparation.

We claim:

1. A piperazine compound of the formula

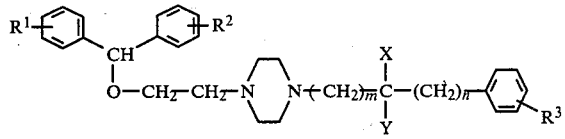

in which

R$^1$ and R$^2$ each represents 1, 2 or 3 halogen atoms, which may be the same or different and are selected from fluorine chlorine and bromine atoms, R$^3$ represents a hydrogen atom or 1, 2 or 3 halogen atoms, X represents a hydroxy, C$_{1-4}$ alkoxy, phenylcarbamoyloxy or C$_{1-4}$ alkylcarbamoyloxy group, Y represents a hydrogen atom or a C$_{1-3}$ alkyl group, or X and Y together with the carbon atom to which they are linked represent a carbonyl group, m is 1, 2 or 3, n is 0 or 1, with the proviso that m+n is at most 3, and their pharmaceutically acceptable acid addition and quaternary ammonium salts.

2. The piperazine derivative according to claim 1, in which R$^1$ and R$^2$ both represent a 4-fluoro atom.

3. The piperazine derivative according to claim 1 or 2, in which R$^3$ represents a 4-fluoro atom.

4. The piperazine derivative according to claims 1 or 2 in which X represents a hydroxyl group.

5. The piperazine derivative according to claim 4, in which Y represents a hydrogen atom.

6. The compound 4-[2-[bis(4-fluorophenyl)methoxy]ethyl]-α-(4-fluorophenyl)-1-piperazinepropanol and its pharmaceutically acceptable acid addition and quaternary ammonium salts.

7. The compound 4-[2-[bis(4-fluorophenyl)methoxy]ethyl]-α-(phenylmethyl)-1-piperazineëthanol and its pharmaceutically acceptable acid addition and quaternary ammonium salts.

8. The compound 4-[2-[bis(4-fluorophenyl)methoxy]ethyl]-α-phenyl-1-piperazinepropanol and its pharmaceutically acceptable acid addition and quaternary ammonium salts.

9. The compound 4-[2-[bis(4-fluorophenyl)methoxy]ethyl]-α-phenyl-1-piperazineëthanol and its pharmaceutically acceptable acid addition and quaternary ammonium salts.

10. The compound 1-[4-[2-[bis(4-fluorophenyl)methoxy]ethyl]-1-piperazinyl]-3-phenyl-2-propanone and its pharmaceutically acceptable acid addition and quaternary ammonium salts.

11. The compound 4-[2-[bis(4-fluorophenyl)methoxy]ethyl]-α-phenyl-1-piperazinebutanol and its pharmaceutically acceptable acid addition and quaternary ammonium salts.

12. The compound 4-[2-[bis(4-fluorophenyl)methoxy]ethyl]-α-(4-fluorophenyl)-α-methyl-1-piperazinepropanol and its pharmaceutically acceptable acid addition and quaternary ammonium salts.

13. The compound 4-[2-[bis(4-fluorophenyl)methoxy]ethyl]-α-phenyl-α-methyl-1-piperazinepropanol and its pharmaceutically acceptable acid addition and quaternary ammonium salts.

14. The compound 4-[2-[bis(4-fluorophenyl)methoxy]ethyl]-α-ethyl-α-phenyl-1-piperazinepropanol and its pharmaceutically acceptable acid addition and quaternary ammonium salts.

15. A dopaminergic pharmaceutical composition comprising, as the active ingredient, a therapeutically effective amount of one or more piperazine derivatives as claimed in one of the claims 1, 2 and 6–14 in combination with a pharmaceutically acceptable carrier.

16. The piperazine derivative according to claim 2 in which X and Y represent a carbonyl group.

17. The piperazine derivative according to claim 2 in which X is a C$_{1-4}$ alkoxy or C$_{1-4}$ alkylcarbamoyloxy group.

18. The piperazine derivative according to claim 3 in which X represents a hydroxyl group.

19. The piperazine derivative according to claim 18 in which R$^3$ represents a hydrogen atom.

* * * * *